(12) United States Patent
Fabinski et al.

(10) Patent No.: US 6,263,722 B1
(45) Date of Patent: Jul. 24, 2001

(54) MAGNETOMECHANICAL GAS ANALYZER, IN PARTICULAR PARAMAGNETIC OXYGEN ANALYZER

(75) Inventors: Walter Fabinski, Kriftel; Thomas Bauer, Bad Homburg, both of (DE)

(73) Assignee: Hartmann & Braun GmbH & Co. KG, Eschborn (DE)

( * ) Notice: Subject to any disclaimer, the term of this patent is extended or adjusted under 35 U.S.C. 154(b) by 0 days.

(21) Appl. No.: 09/393,404

(22) Filed: Sep. 10, 1999

(30) Foreign Application Priority Data

Sep. 12, 1998 (DE) .................................................. 19841723

(51) Int. Cl.$^7$ ............................. G01N 27/74; G01N 27/76
(52) U.S. Cl. .......................... 73/25.02; 324/201; 324/204
(58) Field of Search ................................ 73/25.02, 24.01, 73/31.04; 324/201, 204

(56) References Cited

U.S. PATENT DOCUMENTS

| | | | |
|---|---|---|---|
| 3,612,991 | * 10/1971 | Greene | 324/204 |
| 3,826,974 | * 7/1974 | Kocache et al. | 324/201 |
| 5,369,980 | * 12/1994 | Kocache | 73/25.02 |
| 5,932,794 | * 8/1999 | Fabinski et al. | 73/25.02 |

* cited by examiner

Primary Examiner—Hezron Williams
Assistant Examiner—Jay L. Politzer
(74) Attorney, Agent, or Firm—Michael M. Rickin

(57) ABSTRACT

A magnetomechanical gas analyzer such a paramagnetic oxygen analyzer which has a dumbbell which is rotatably suspended in the region of action of an inhomogeneous magnetic field and around which a gas to be measured flows. The dumbbell is connected, fixed in rotation, to a mirror for deflecting a light beam. In order to damp in the analyzer all kinds of oscillations which have a negative effect on stability in the balance point, and to increase the detectability and the speed of the measurement, there are least two electrically conductive surface segments which are essentially perpendicular to one another are arranged for eddy-current damping on the dumbbell or in the mechanical gearing on the dumbbell and in the region of action of the inhomogeneous magnetic field. One of the surface segments may be the mirror.

30 Claims, 1 Drawing Sheet

MAGNETOMECHANICAL GAS ANALYZER, IN PARTICULAR PARAMAGNETIC OXYGEN ANALYZER

FIELD OF THE INVENTION

This invention relates to a magnetomechanical gas analyzer and more particularly to a paramagnetic gas analyzer such as an oxygen analyzer which has a dumbbell that is rotatably suspended in the region of action of an inhomogeneous magnetic field and around which a paramagnetic gas to be measured flows and to the damping of all of the oscillations that have a negative effect on the stability of the analyzer's balance point.

DESCRIPTION OF THE PRIOR ART

Gas analyzers that have a dumbbell that is rotatably suspended in the region of action of an inhomogeneous magnetic field use the paramagnetic property of a gas such as oxygen and in effect exploit the deflection of paramagnetic gas in the inhomogeneous field.

In known arrangements of this kind, a diamagnetic dumbbell is rotatably suspended from a taut band in an inhomogeneous field. In the presence of a paramagnetic gas, such as oxygen, the body of the dumbbell is pushed out of the magnetic field. With the aid of a compensating coil, the dumbbell is turned back into its initial position. The current needed for this is a measure of the oxygen concentration in the gas to be measured flowing around the dumbbell. The rotation or counter-rotation is in this case made visible or recordable by a system involving a light beam and a mirror.

The limiting factors for the performance of this measurement method are the detectability and the speed of the measurement. The smallest possible detectable or resolvable measurement range in this case is physically dictated by the instability of the dumbbell at the balance point. The speed of the measurement essentially depends on finding the aforementioned balance point rapidly.

As an example of analyzers of the known type, DE 2339960 discloses a gas detector in which two-dimensional oversizing of the conductor tracks is provided on the body of the dumbbell and in its plane, these regions acting as eddy-current brakes under the influence of the magnetic field. Rotational oscillations about this plane are thereby damped.

However, because of shaking or vibrations which the instrument experiences, there are also oscillations in other planes. A fundamental aspect of this is that vibrational oscillations which also affect the dumbbell and cause the aforementioned instability about the balance point are a sum of linearly independent individual oscillations which from a mathematical standpoint are made up of orthogonal oscillation components. This in turn means that damping only in one oscillation plane cannot lead to any damping action of an oscillation component in a respectively orthogonal plane.

On the basis of this, the present invention dampens oscillations of all kinds which have a negative effect on stability at the balance point and increases detectability and the speed of the measurement.

SUMMARY OF THE INVENTION

The present invention uses an eddy-current brake, to settle or obtain damped motion of the dumbbell, not only in one plane, that is to say the rotational plane of the dumbbell, but also damps other oscillation planes.

This use of an eddy-current brake is based on the discovery that perpendicular oscillation planes are mathematically and physically independent of one another, so that damping in one plane does not give any damping coupling to any other of the oscillation planes. To that end, at least two electrically conductive surface segments which are essentially perpendicular to one another are arranged for eddy-current damping on the dumbbell or in the mechanical gearing on the dumbbell and in the region of action of the inhomogeneous field. The inhomogeneous magnetic field which is present has in this case field components in almost all directions. The effect of this is that magnetic action also acts on the different planes, or the eddy-current surfaces lying in different planes. This means that only one magnetic field arrangement is needed even in this case.

Consequently, efficient eddy-current induction takes place, resulting from oscillations of at least two spatial direction components. This means that considerably more effective damping in the region of the aforementioned balance point is possible.

In a further advantageous refinement, one of the electrically conductive surface segments is formed with a mirror surface which is applied or vapor deposited. This mirror surface is in this case effective as an eddy-current brake for the oscillation component lying perpendicular to the plane of the mirror. In this embodiment, the dumbbell is advantageously produced in micromechanical silicon technology or in glass.

In both embodiments, the mirror surface can be vapor deposited in a straightforward way by processes that use either PVD or CVD technology. The thickness of the vapor deposited mirror surface should be dimensioned such that it is possible to generate a current density which is required in terms of eddy-current braking in this space plane.

The other metallic surface, which acts as another eddy-current brake and is perpendicular to the mirror surface, is formed in the region of the current paths on the dumbbell. Further, the material for the eddy-current brake is advantageously a chemically stable material. Particularly suitable examples include platinum, rhodium, rhenium, aluminum, titanium or nickel.

DESCRIPTION OF THE PREFERRED EMBODIMENT(s)

Figure 1:
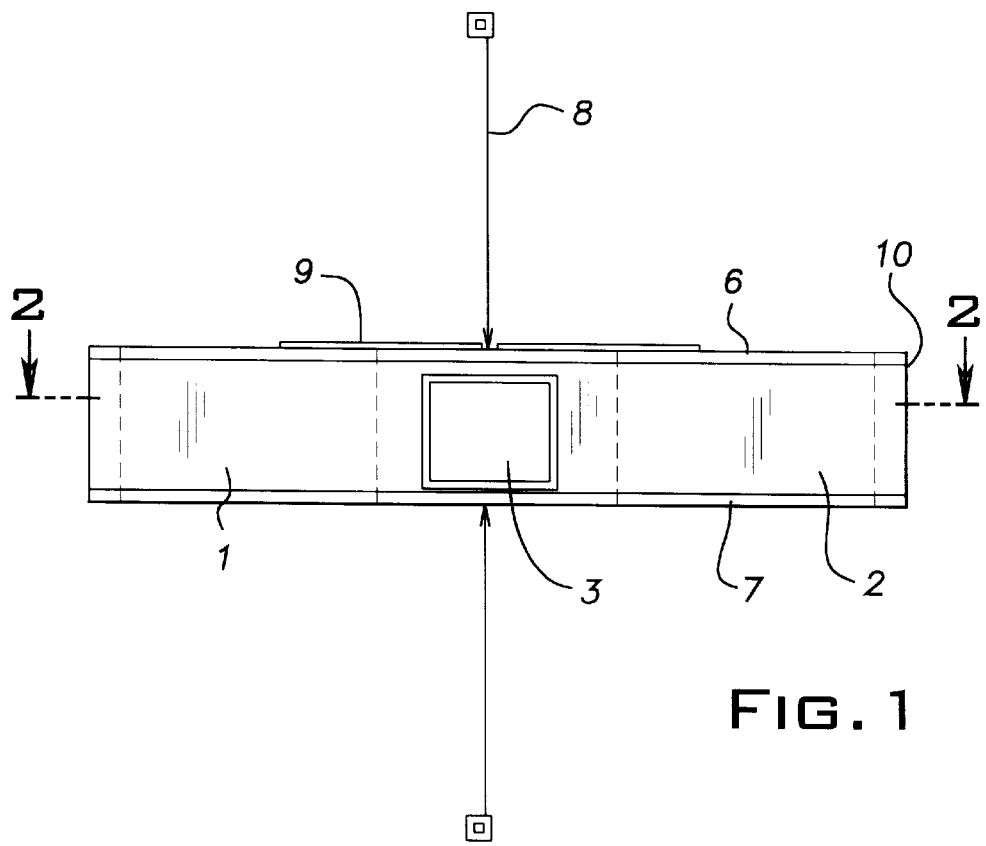
FIG. 1 shows a dumbbell with a mirror surface.

FIG. 1 shows the aforementioned dumbbell body 10 in a side view in which the applied mirror 3 can be seen. The dumbbell 10 itself is surrounded by an inhomogeneous magnetic field, not represented in detail here. The mirror 3 deflects a light beam, not shown, which provides an indication of the rotation of the dumbbell 10 and therefore the concentration of paramagnetic gas. The dumbbell 10 is rotatably suspended from mechanical filament 8. The dumbbell has body sections 1 and 2 inside of which are volumes 11 and 12 (see FIG. 2) which as is well known in the art each contain a reference gas.

The dumbbell 10 may in this case, as described above, either be made in micromechanical silicon technology or be made of glass. In both cases, the mirror surface 3 is applied using either the PVD or CVD technique. The mirror surface 3 is in this case perpendicular to the other eddy-current surface 9, which lies in the region of the current paths of the balancing coil either on the bottom plate 7 or the top plate 6. Surface 9 is shown in FIG. 1 on top plate 6.

The applied mirror surface 3 and the eddy-current surface 9 provide two eddy-current surfaces which are perpendicular to each other and can accordingly damp even two space-directional components of oscillations which occur. It is entirely possible to provide yet another third eddy-current surface so that all three space directions or space planes are covered in terms of damping. The third eddy-current surface would be on the two ends 13, 14 of the dumbbell 10.

Figure 2:
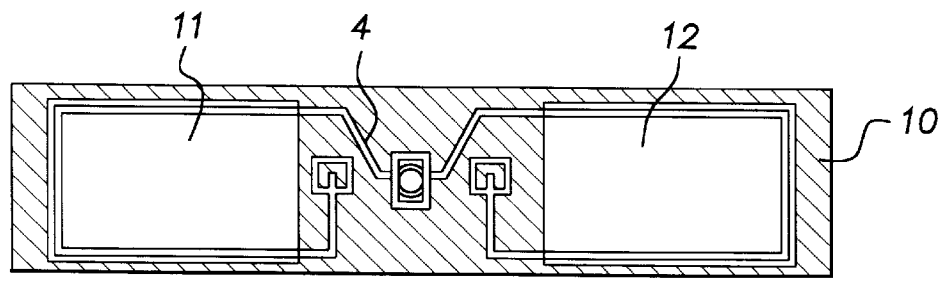
FIG. 2 shows section A–B according to FIG. 1, in plan view.

FIG. 2 shows the dumbbell 10 in a plan view on section A–B in FIG. 1 of the balancing coil 4 and its current paths. There is also one of the effective eddy-current surfaces in the vicinity of this, or parallel thereto, such as the surface 9 shown in FIG. 1.

It is to be understood that the description of the preferred embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A magnetomechanical gas analyzer comprising:
   a. a dumbbell which is rotatably suspended in the region of action of an inhomogeneous magnetic field and around which a gas to be measured flows, said dumbbell being connected, fixed in rotation, to a mirror for deflecting a light beam; and
   b. at least two electrically conductive surface segments which are essentially perpendicular to one another are arranged for eddy-current damping on said dumbbell and in said region of action of said inhomogeneous magnetic field.

2. The magnetomechanical gas analyzer of claim 1, wherein one of said at least two electrically conductive surface segments is said mirror which is fitted metal and dimensioned in terms of thickness such that it is possible to generate a current density which is required in terms of eddy-current damping in this space plane.

3. The magnetomechanical gas analyzer of claim 1 wherein said dumbbell is made in micromechanical silicon technology.

4. The magnetomechanical gas analyzer of claim 2 wherein said dumbbell is made in micromechanical silicon technology.

5. The magnetomechanical gas analyzer of claim 1 wherein said dumbbell is made of glass.

6. The magnetomechanical gas analyzer of claim 2 wherein said dumbbell is made of glass.

7. The magnetomechanical gas analyzer of claim 3 wherein said mirror as well as another of said at least two electrically conductive surface segments which is arranged in the plane of the conductive current paths on said dumbbell are applied by using PVD technology.

8. The magnetomechanical gas analyzer of claim 4 wherein said mirror as well as another of said at least two electrically conductive surface segments which is arranged in the plane of the conductive current paths on said dumbbell are applied by using PVD technology.

9. The magnetomechanical gas analyzer of claim 5 wherein said mirror as well as another of said at least two electrically conductive surface segments which is arranged in the plane of the conductive current paths on said dumbbell are applied by using PVD technology.

10. The magnetomechanical gas analyzer of claim 6 wherein said mirror as well as another of said at least two electrically conductive surface segments which is arranged in the plane of the conductive current paths on said dumbbell are applied by using PVD technology.

11. The magnetomechanical gas analyzer of claim 3 wherein said mirror as well as another of said at least two electrically conductive surface segments which is arranged in the plane of the conductive current paths on said dumbbell are applied by using CVD technology.

12. The magnetomechanical gas analyzer of claim 4 wherein said mirror as well as another of said at least two electrically conductive surface segments which is arranged in the plane of the conductive current paths on said dumbbell are applied by using CVD technology.

13. The magnetomechanical gas analyzer of claim 5 wherein said mirror as well as another of said at least two electrically conductive surface segments which is arranged in the plane of the conductive current paths on said dumbbell are applied by using CVD technology.

14. The magnetomechanical gas analyzer of claim 6 wherein said mirror as well as another of said at least two electrically conductive surface segments which is arranged in the plane of the conductive current paths on said dumbbell are applied by using CVD technology.

15. The magnetomechanical gas analyzer of claim 1 wherein said at least two electrically conductive surface segments are made of platinum, rhodium, rhenium, aluminum, titanium or nickel.

16. The magnetomechanical gas analyzer of claim 2 wherein said at least two electrically conductive surface segments are made of platinum, rhodium, rhenium, aluminum, titanium or nickel.

17. The magnetomechanical gas analyzer of claim 3 wherein said at least two electrically conductive surface segments are made of platinum, rhodium, rhenium, aluminum, titanium or nickel.

18. The magnetomechanical gas analyzer of claim 4 wherein said at least two electrically conductive surface segments are made of platinum, rhodium, rhenium, aluminum, titanium or nickel.

19. The magnetomechanical gas analyzer of claim 5 wherein said at least two electrically conductive surface segments are made of platinum, rhodium, rhenium, aluminum, titanium or nickel.

20. The magnetomechanical gas analyzer of claim 6 wherein said at least two electrically conductive surface segments are made of platinum, rhodium, rhenium, aluminum, titanium or nickel.

21. The magnetomechanical gas analyzer of claim 7 wherein said at least two electrically conductive surface segments are made of platinum, rhodium, rhenium, aluminum, titanium or nickel.

22. The magnetomechanical gas analyzer of claim 8 wherein said at least two electrically conductive surface segments are made of platinum, rhodium, rhenium, aluminum, titanium or nickel.

23. The magnetomechanical gas analyzer of claim 9 wherein said at least two electrically conductive surface segments are made of platinum, rhodium, rhenium, aluminum, titanium or nickel.

24. The magnetomechanical gas analyzer of claim 10 wherein said at least two electrically conductive surface segments are made of platinum, rhodium, rhenium, aluminum, titanium or nickel.

25. The magnetomechanical gas analyzer of claim 11 wherein said at least two electrically conductive surface segments are made of platinum, rhodium, rhenium, aluminum, titanium or nickel.

26. The magnetomechanical gas analyzer of claim 12 wherein said at least two electrically conductive surface segments are made of platinum, rhodium, rhenium, aluminum, titanium or nickel.

27. The magnetomechanical gas analyzer of claim 13 wherein said at least two electrically conductive surface segments are made of platinum, rhodium, rhenium, aluminum, titanium or nickel.

28. The magnetomechanical gas analyzer of claim 14 wherein said at least two electrically conductive surface segments are made of platinum, rhodium, rhenium, aluminum, titanium or nickel.

29. The magnetomechanical gas analyzer of claim 1 wherein said gas analyzer is a paramagnetic oxygen analyzer.

30. The magnetomechanical gas analyzer of claim 1 wherein said at least two electrically conductive surface segments are in the mechanical gearing of said dumbbell.

* * * * *